(12) United States Patent
De La Torre Barreiro

(10) Patent No.: US 11,229,803 B2
(45) Date of Patent: Jan. 25, 2022

(54) DEVICE FOR TREATING ARTHRITIS AND OSTEOARTHRITIS IN EXTREMITIES AND CHRONIC INFLAMMATIONS AND FOR REDUCING MUSCULAR PAIN AND TENSION

(71) Applicant: DEMAC, S.A., Boadilla del Monte (ES)

(72) Inventor: Jose Luis De La Torre Barreiro, Madrid (ES)

(73) Assignee: DEMAC, S.A., Boadilla del Monte (ES)

( * ) Notice: Subject to any disclaimer, the term of this patent is extended or adjusted under 35 U.S.C. 154(b) by 426 days.

(21) Appl. No.: 16/072,795

(22) PCT Filed: Jan. 25, 2016

(86) PCT No.: PCT/ES2016/070040
§ 371 (c)(1),
(2) Date: Jul. 25, 2018

(87) PCT Pub. No.: WO2017/032910
PCT Pub. Date: Mar. 2, 2017

(65) Prior Publication Data
US 2018/0361167 A1    Dec. 20, 2018

(51) Int. Cl.
*A61N 1/40*     (2006.01)
*A41D 19/015*   (2006.01)
(Continued)

(52) U.S. Cl.
CPC .......... *A61N 1/40* (2013.01); *A41D 19/01535* (2013.01); *A41D 19/01588* (2013.01);
(Continued)

(58) Field of Classification Search
CPC ..... A61H 33/04; A61H 2033/047; A61F 7/00; A61F 5/0118; A61F 5/05875; A61F 5/10;
(Continued)

(56) References Cited

U.S. PATENT DOCUMENTS 3,513,842 A * 5/1970 Berg ...................... A61F 5/0109
                                                          602/60
4,662,006 A * 5/1987 Ross, Jr. ................. A41D 19/01
                                                          2/158
(Continued)

FOREIGN PATENT DOCUMENTS

AU    4394989 A      5/1990
CN    201210876 Y *  3/2009  ........... A41D 19/015
(Continued)

OTHER PUBLICATIONS

Machine translation from espacenet of CN 201210876 Y (Year: 2009).*
International Search Report dated May 20, 2016.

*Primary Examiner* — Alireza Nia
*Assistant Examiner* — Kevin S Albers
(74) *Attorney, Agent, or Firm* — William H. Honaker; Dickinson Wright PLLC

(57) ABSTRACT

Device for the treatment of arthritis and arthrosis of the extremities generally shaped as a case, in the form of a glove or a sock, which comprises: an inner layer made of a porous material (14); a second layer in the form of a paraffin-filled bladder (1) that covers the entire inner space; surrounding said inner paraffin layer (1), the following are placed: a Polytetrafluoroethylene splint (2) equipped with means designed to straighten the fingers or toes (wires made of nitinol or a similar material); a very thin layer made of latex or an insulating material (4); and, finally, an outer cover (6); it may further be equipped with wires or coils (5) around each finger or parallel to the palm or the back of the hand.

(Continued)

Moreover, it is equipped with a control unit (12) for turning on and for controlling the temperatures and currents to be applied.

10 Claims, 4 Drawing Sheets

(51) Int. Cl.
*A61F 7/00* (2006.01)
*A61F 7/02* (2006.01)
*A61N 1/36* (2006.01)
*A61F 5/01* (2006.01)
*C22C 19/03* (2006.01)
*C09K 5/00* (2006.01)
*A61B 17/00* (2006.01)
*A61N 1/04* (2006.01)

(52) U.S. Cl.
CPC ...... *A41D 19/01594* (2013.01); *A61F 5/0118* (2013.01); *A61F 7/00* (2013.01); *A61F 7/007* (2013.01); *A61F 7/02* (2013.01); *A61N 1/0452* (2013.01); *A61N 1/0472* (2013.01); *A61N 1/3603* (2017.08); *A61N 1/36021* (2013.01); *C09K 5/00* (2013.01); *C22C 19/03* (2013.01); *A61B 2017/00867* (2013.01); *A61F 2005/0155* (2013.01); *A61F 2007/0036* (2013.01); *A61F 2007/0045* (2013.01); *A61F 2007/0071* (2013.01); *A61F 2007/0233* (2013.01); *A61F 2007/0292* (2013.01)

(58) Field of Classification Search
CPC ...... A61F 5/013; A61F 5/019; A61F 5/05866; A61F 7/007; A61F 7/02; A61F 2005/0155; A61F 2007/0036; A61F 2007/0045; A61F 2007/0071; A61F 2007/0233; A61F 2007/0292; A61F 2007/0078; A61F 2007/0244; A61F 2/4225; A61F 5/00; A61F 5/01; C22C 19/03; C09K 5/00; A61N 1/36021; A61N 1/0472; A61N 1/0452; A61N 1/3603; A61N 1/40; A41D 19/01535; A41D 19/01588; A41D 19/01594; A61B 2017/00867; A61B 2017/606; A61B 17/66; G06F 3/017; G06F 3/014; G06F 3/013
USPC .......................................................... 602/2
See application file for complete search history.

(56) References Cited

U.S. PATENT DOCUMENTS

| | | | | |
|---|---|---|---|---|
| 4,964,402 | A | * | 10/1990 | Grim ................... A61F 5/0111 602/2 |
| 5,160,828 | A | * | 11/1992 | Olsen ..................... A61F 7/007 219/211 |
| 6,146,413 | A | | 11/2000 | Harman |
| 2006/0094989 | A1 | * | 5/2006 | Scott ...................... A61F 2/586 601/5 |
| 2008/0223844 | A1 | * | 9/2008 | Cronn ............. A41D 19/01535 219/211 |
| 2010/0268136 | A1 | * | 10/2010 | Der Ovanesian ..... A61F 5/0104 602/14 |
| 2012/0065026 | A1 | * | 3/2012 | Land .................. A63B 21/4025 482/47 |
| 2016/0095369 | A1 | * | 4/2016 | Roberts ........... A41D 19/01535 2/160 |
| 2016/0235139 | A1 | * | 8/2016 | Gramlin .......... A41D 19/01535 |
| 2017/0056229 | A1 | * | 3/2017 | Palmer ................... A61F 5/019 |

FOREIGN PATENT DOCUMENTS

| | | | | |
|---|---|---|---|---|
| CN | 201210876 | Y | * 5/2009 | ........... A41D 19/015 |
| DE | 102008003124 | A1 | 7/2009 | |
| KR | 20070096208 | A | 10/2007 | |
| WO | 9853264 | A1 | 11/1998 | |

* cited by examiner

DEVICE FOR TREATING ARTHRITIS AND OSTEOARTHRITIS IN EXTREMITIES AND CHRONIC INFLAMMATIONS AND FOR REDUCING MUSCULAR PAIN AND TENSION

CROSS-REFERENCE TO RELATED APPLICATION

The present invention claims priority to PCT International Patent Application Serial No. PCT/ES2016/070040 filed Jan. 25, 2016, the entire disclosure of the application being considered part of the disclosure of this application and hereby incorporated by reference.

OBJECT OF THE INVENTION

As the title of the invention specifies, the object of the present invention is a device for the treatment of arthritis and arthrosis of the extremities, chronic inflammations, pain reduction and muscle tension, in the form of a glove or a sock which, placed on the extremities, makes it possible to treat arthritis and arthrosis of said extremities in a rapid and efficient manner.

The present invention is characterised by the constructive characteristics of the device, which makes it possible to simultaneously combine, within the same device, different techniques and means, with the consequent synergistic result arising from the simultaneous arrangement and use of different techniques.

Therefore, the present invention is framed within the scope of devices and techniques used in the treatment of arthritis, arthrosis, chronic inflammations, pain reduction and muscle tension in the extremities.

BACKGROUND OF THE INVENTION

Arthrosis is a degenerative disease caused by the deterioration of the articular cartilages, which are those parts that cover the ends of the bones and, bound to one another, form the joints, the components of the skeleton that make movement possible.

Articular cartilages are essential for a good functioning of the joints, since they are the cushioning and sliding surfaces between the ends of the bones that compose all joints.

During the development of the disease, the erosion of an articular cartilage may alter the articular cartilage of the bone opposite the joint, resulting in the beginning of the wearing process.

As a consequence, at some point the cartilages may disappear and pain will appear. As the cartilage progressively disappears, the bone reacts and grows on the sides (osteophytes), thereby causing deformation of the joint.

On the other hand, arthritis is inflammation of the joints and causes pain and stiffness; it affects a large number of people, particularly as they get older.

There is a variety of treatments for arthrosis and arthritis, including customised, adapted exercise plans and pharmacological treatments.

There are other treatments, such as paraffin baths, a superficial thermotherapy method for the treatment of arthrosis and arthritis, amongst other conditions.

The therapeutic agent in paraffin baths is heat; for this reason, in order to prepare them, it is necessary for the substance to reach a temperature ranging between 50 and 54 degrees Celsius. The calorific value of paraffin baths is six times greater than that of water and the analgesia obtained is greater and longer-lasting.

The first step is to introduce the hand into a paraffin container at the aforementioned temperature for a few seconds, between 6 and 12 times, and then remove the hand from the bath and wait between 15 and 20 minutes, until the paraffin cools down and forms a solid layer. A mitt may be used at this stage.

Paraffin wax has a low melting point, low enough such that it may be applied to the skin without the risk of burning. The heat sensation of the melted wax relieves the pain caused by arthritis, by loosening the muscles, increasing the blood flow and relaxing the hands. Moreover, essential oils may be added, which help to relieve the pain and promote relaxation.

Other techniques used in the treatment of arthrosis and arthritis include cold and heat therapy and electrotherapy.

Cold therapy is only indicated when there is a phase of acute inflammation of the joint, whereas the application of heat is intended to relieve the pain, the joint stiffness and the muscle contractions caused by arthrosis.

Electrotherapy involves the application of electric, magnetic or combined fields with a given frequency and intensity, such that they activate the damaged area. One electrotherapy technique is shortwave therapy, which is designed to achieve an increase in temperature, in order to cause an increase in circulation and fluidification, which, in turn, results in increased tissue regenerative capacity; moreover, the tissues can move more easily due to the increased elasticity and fluidity.

Another technique used for articular health improvement in the case of arthrosis and arthritis involves using stack splints, the purpose whereof is to immobilise the distal interphalangeal joint by keeping it extended or hyperextended, whilst allowing for movement of the proximal interphalangeal joint, thereby preventing potential adverse effects on the rest of the joints.

It is also known in the state of the art the patent CN 201210876Y which discloses an electrothermal olefin chilblain preventing and treating glove, which comprises a glove body and a heating control device. The electrothermal olefin chilblain preventing glove is characterized in that the inside of the glove body is provided with a sealed interlayer; the inside of the sealed interlayer is provided with an olefin layer; the inside of the olefin layer is provided with one or more than one heating block.

All of the aforementioned techniques must be applied separately and in multiple sessions; moreover, they are applied by professionals using costly, complex machinery; for these reasons, the treatment of said conditions is costly in terms of time, money and dedication on the part of the patients.

Therefore, the object of the present invention is to develop a device that makes it possible to simultaneously apply the aforementioned techniques, in any combination, in a simple, effective manner, without the need to visit a specialised centre to receive said treatment, by developing a device such as the one described below, which is essentially explained in the first claim.

DESCRIPTION OF THE INVENTION

The object of the present invention is a device for the treatment of arthrosis, arthritis, chronic inflammations, pain reduction and muscle tension, which in general has the shape of a case, such as a glove or a sock, that houses the extremity to be protected.

The device comprises a number of layers or elements, which, from the inside to the outside, are arranged as follows:

A first inner layer made of a porous material

A second inner layer or volume in the form of a paraffin-filled bladder, which covers the entire inner space or, partially, the specific areas targeted for treatment A splint made of Polytetrafluoroethylene or a semi-rigid material in the form of a stack splint wherein the second paraffin layer is housed. These Polytetrafluoroethylene or similar splints force the finger or toe to progressively straighten. The adjustment may be performed by means of tensors, brackets or magnets on both sides under traction.

Wires made of nitinol (an alloy of titanium and nickel or similar) or a similar material, which are capable of returning to the original shape due to the thermoplastic martensitic transformation between an austenitic phase and a martensitic phase. They have great flexibility, biocompatibility with human beings, and are not corrosive. As the temperature rises, the dimensions change and, when the temperature changes, they recover the original dimensions. Materials similar to Nitinol include bimetals. In the most simple embodiment, these materials which have the property of changing their length as a function of temperature fulfil the following functions:

Heating the paraffin

Generating an electromagnetic field for shortwave treatment, longwave treatment, etc.

Acting as stack cell promoters in order to straighten the extremities.

A very thin layer made of latex or an insulating material covering all the aforementioned elements.

Finally, an outer layer of the glove that covers all of the above.

Additionally, in a complementary manner, heating wires or coils made of woven carbon fibres, or an electrically resistive element, such as, for example, metal wires, may be placed surrounding said insulating layer, or inside the paraffin bladder, such that, when heated to a given temperature, they melt the paraffin inside, and may also act as electromagnetic field generators.

These carbon fibre heating wires or coils may be placed around the fingers or parallel to the plane formed by the palm and the back of the hand, in order to generate electromagnetic fields perpendicular to the hand.

Therefore, the invention relates to a device in the form of a case, for example, a glove or a sock, with independent fingers or toes, which is equipped with an inner paraffin case heated by means of resistive coils, which may further be used to apply electrotherapy, shortwave or electromagnetic fields with different wavelengths.

Moreover, thanks to the Polytetrafluoroethylene splints, in the form of stack splints, the articular position may be simultaneously corrected.

Furthermore, in the case that wires made of Nitinol or other bimetallic materials are used, the straightening effect on the articular joints is reinforced, thanks to the property of changing their dimensions with increased temperature and subsequently recovering their position.

Therefore, thanks to the constructive characteristics of the device, several techniques may be simultaneously applied, either completely or by combining some of them; moreover, this allows for use during sleep or without conducting any particular activity that requires using the hands, such that visits to a specialised centre or using complex machinery for the application thereof are not required, which effectively and radically improves the treatment of arthrosis and arthritis, chronic inflammations, pain reduction and muscle tension.

Except as otherwise specified, all the technical and scientific elements used in the present specification have the habitual meaning understood by normal persons skilled in the art whereto this invention pertains. When implementing the present invention, similar or equivalent processes and materials to those described in the specification may be used.

Throughout the description and the claims, the word "comprises" and variants thereof are not intended to exclude other technical characteristics, additives, components or steps. For persons skilled in the art, other objects, advantages and characteristics of the invention will arise, partly from the description and partly from the practice of the invention.

DESCRIPTION OF THE FIGURES

In order to supplement the description being made, and contribute to a better understanding of the characteristics of the invention, according to a preferred embodiment thereof, a set of drawings is attached, as an integral part of said description, wherein the following is represented, for illustrative, non-limiting purposes.

PREFERRED EMBODIMENT OF THE INVENTION

In light of the figures, below we describe a preferred embodiment of the proposed invention.

Figure 1:
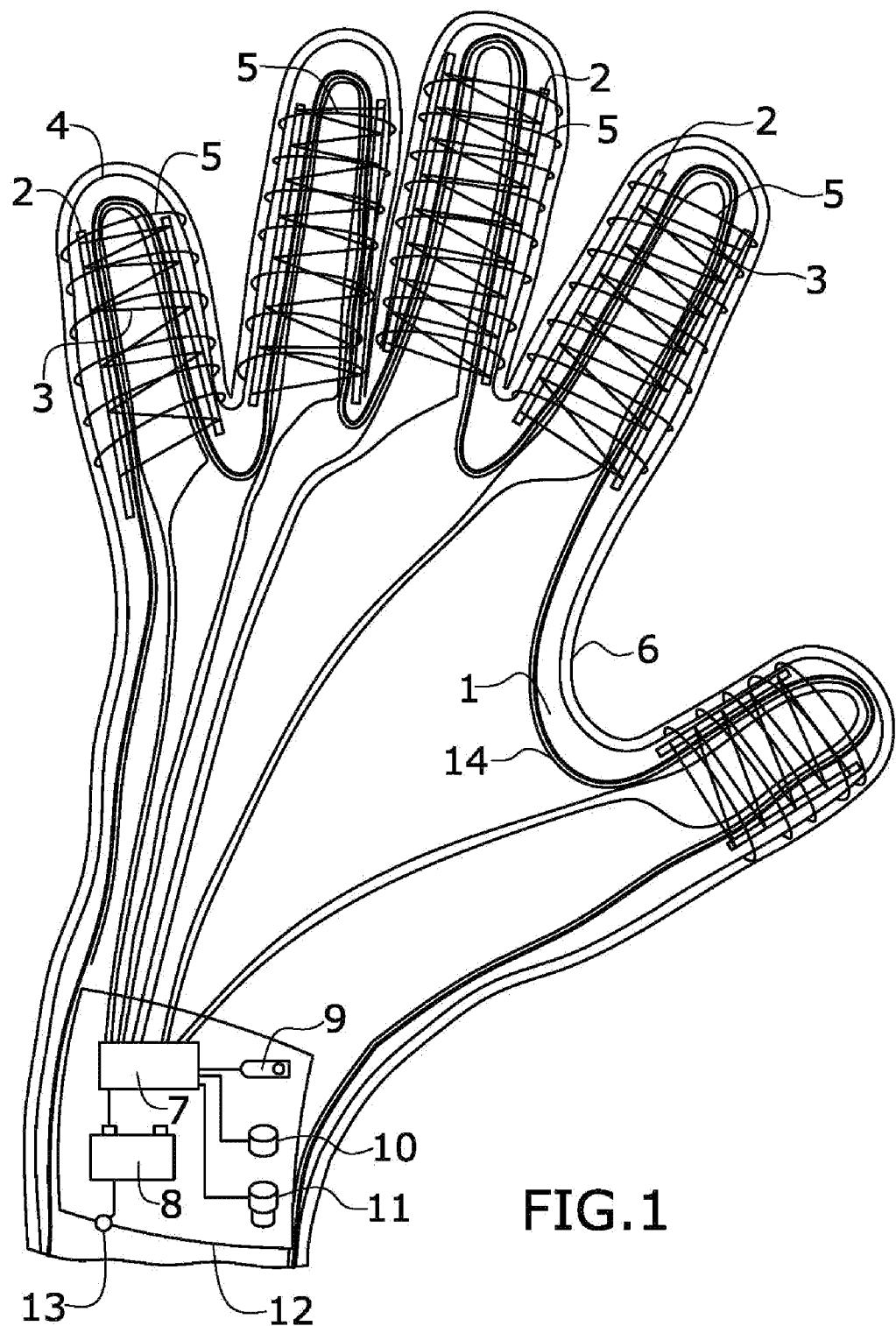
FIG. 1 shows a simplified representation of a device in the shape of the glove, with a representation of the elements that form a part of it.

In FIG. 1, we may observe that the device of the invention comprises:

A first inner layer (14) made of a porous material

A second inner layer or volume in the form of a paraffin-filled bladder (1), which covers the entire inner space or, partially, the areas targeted for treatment.

Said second inner paraffin layer or volume (1) is surrounded by a Polytetrafluoroethylene or similar splint (2) in the form of a stack splint. These Polytetrafluoroethylene or similar splints are equipped with means that force the finger to progressively straighten. The adjustment may be performed by means of tensors, brackets or magnets on both sides under traction.

A very thin layer made of latex or an insulating material (4).

An outer cover (6) that surrounds all the aforementioned layers.

In a first embodiment, the means with which the splints (2) are equipped to progressively straighten the wire comprise wires made of Nitinol (3) or bimetallic materials arranged in a spiral design or fixed to the upper opening of the stack splints, wherein the wires made of Nitinol or bimetallic materials, as indicated, may change their dimensions when the temperature increases and, subsequently, if the temperature is reduced, recover the initial position.

These wires that change their dimensions as a function of temperature fulfil a triple function:
Heating the paraffin
Generating an electromagnetic field, for shortwave treatment, longwave treatment, etc.
Acting as stack cell promoters, in order to straighten the extremities.

In a possible complementary embodiment, in addition to the nitinol or similar wires (3), the device may be equipped with wires or coils (5) preferably made of woven carbon, nichrome, nitinol or any other conductive element, such that, when heated to a certain temperature, the paraffin melts.

These wires or coils (5) may be placed between the thin insulating or latex layer (4) and the outer wrapping, or inside the second outer paraffin layer or volume.

Said wires or coils (5) may be placed around each finger or as reels parallel to the back and the palm of the hand.

Moreover, they may have the double function of generating heat to melt the paraffin or electromagnetic fields to generate short waves.

Furthermore, the device is equipped with a control unit (12) for turning on and controlling the temperatures and currents to be applied.

Figure 2:
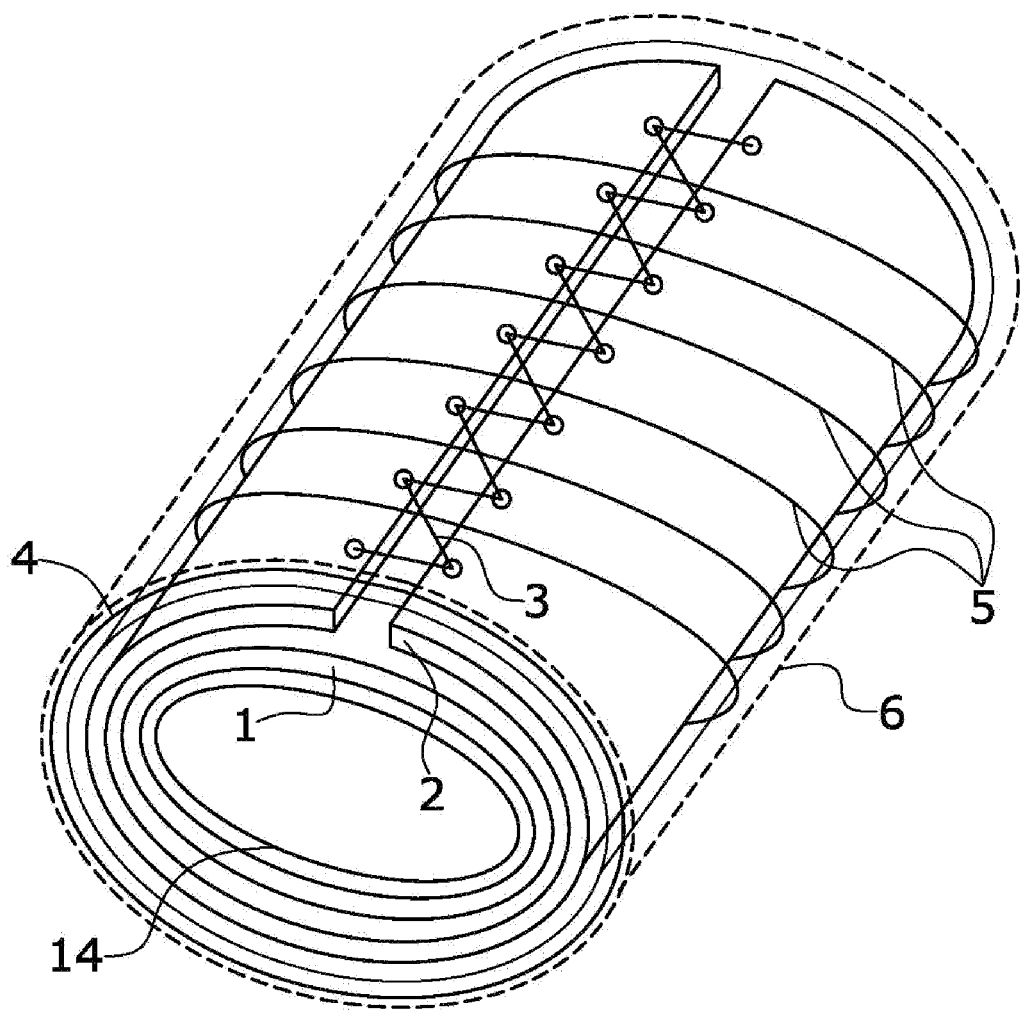
FIG. 2 shows a detailed example of one of the cavities of the device, in order to show in a detailed manner the elements that make it up and their relative positions.

FIG. 2 shows a possible embodiment of the section of a cavity designed to house a finger or a toe, wherein the nitinol wires (3) are fixed to the free edge of the splint (2) and, when subjected to an increase in temperature, for example caused by the resistive coils (4), reduce the splint diameter (2); for illustrative purposes, the free inner diameter of said splint with the nitinol wires (3) at a temperature ranging between 25° C. and 30° C. is 16 mm, whereas the diameter of said splint with the nitinol wires at 45° C. decreases to 12 mm, which leads to a straightening process of the joints inside due to the reduction in the free inner space.

The control unit (12) of the device comprises:
a switch (9) for programme selection and turning on and off
a temperature remote control (10)
a current remote control (11) for the electrotherapy application.
An electronic circuit (7) wherein all the circuits directed to each of the fingers or toes are controlled.
Supply means, which may be connected to a distribution network or, in the form represented, include a rechargeable battery (8), and are equipped with a charging point (13) from the power supply network.

Figure 3:
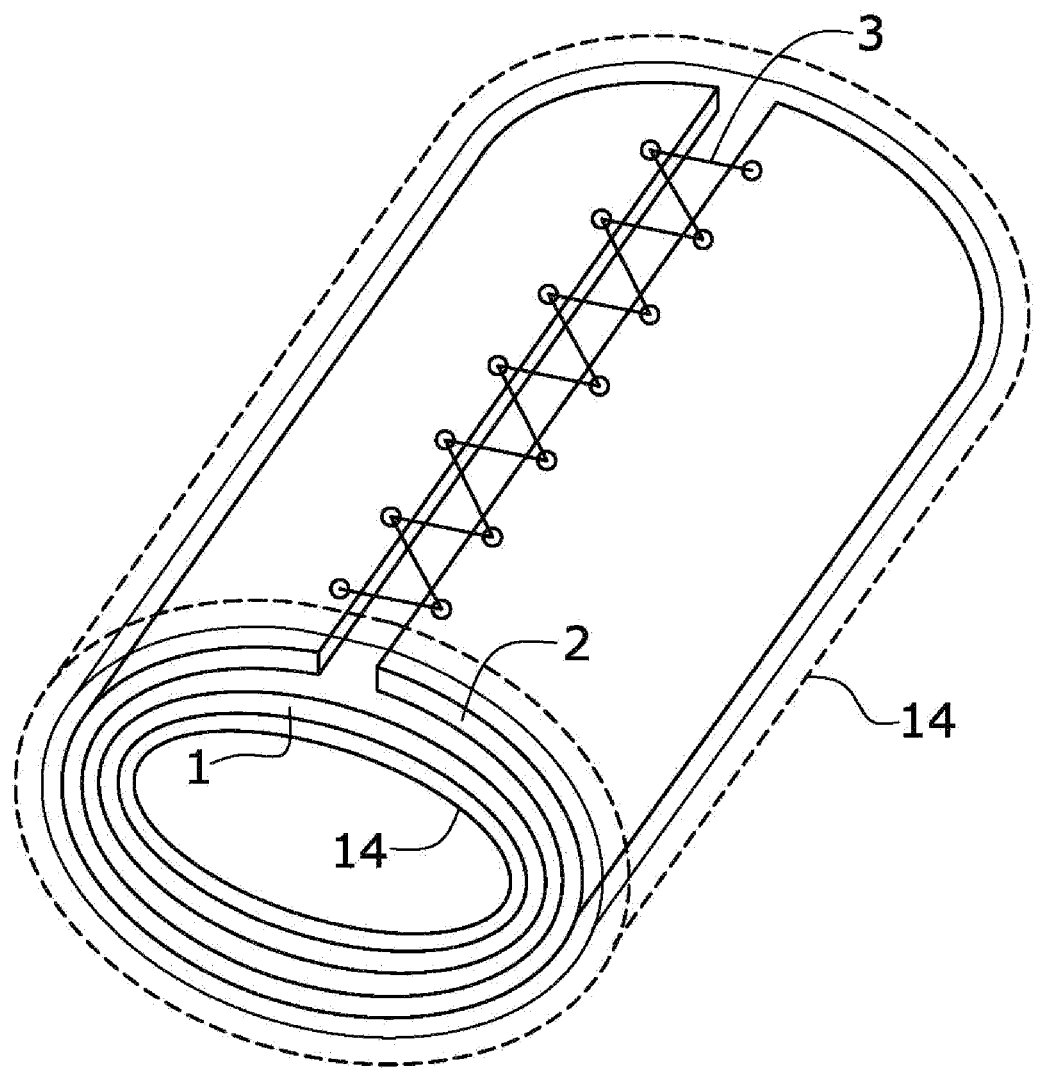
FIG. 3 shows an embodiment wherein the coils are housed or embedded inside the second inner layer or volume in the form of a paraffin-filled bladder.
Figure 4:
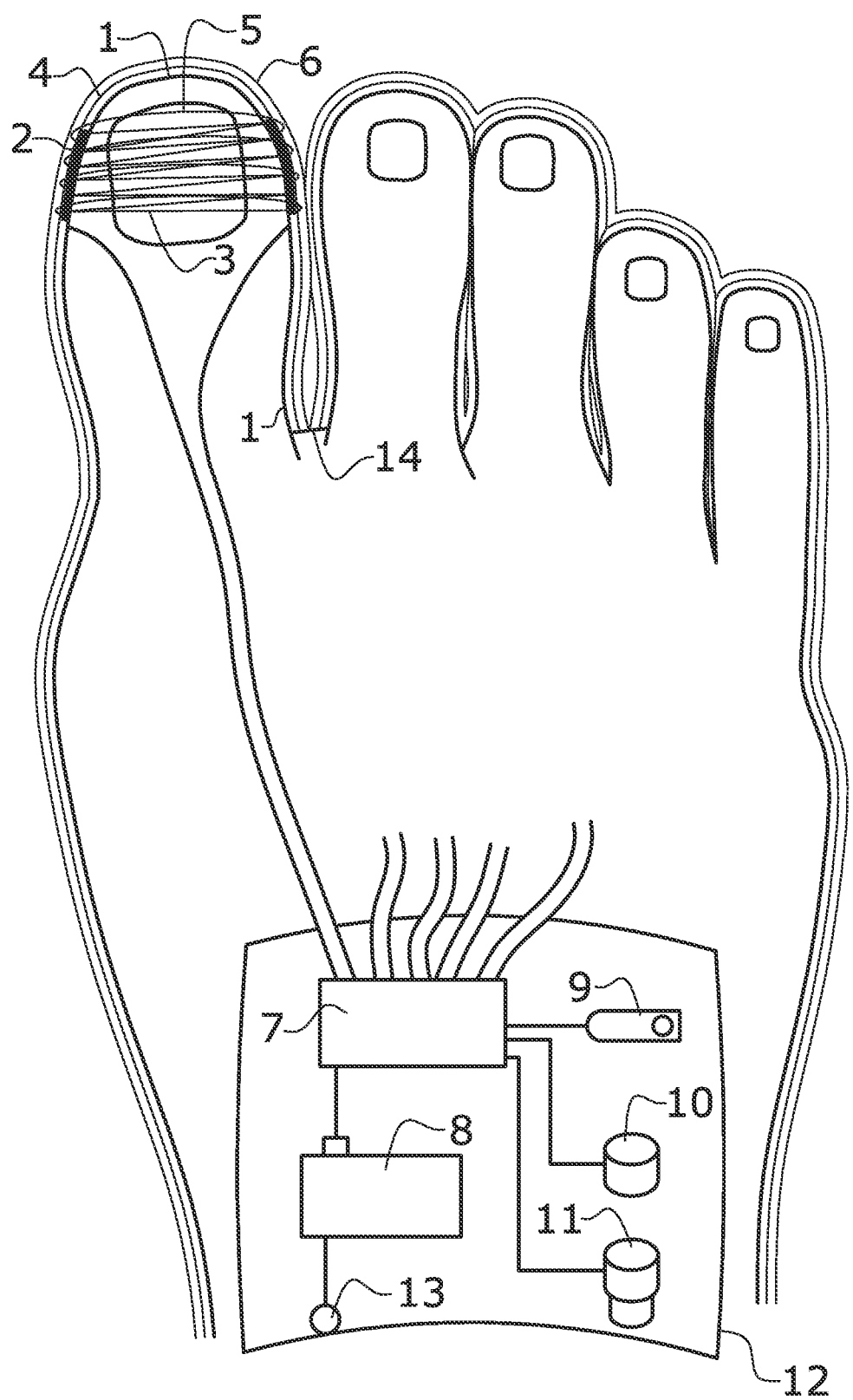
FIG. 4 shows a simplified representation of a device in the shape of a sock, with a representation of the elements that form a part of it.

FIG. 3 shows an alternative embodiment wherein, instead of surrounding the splint made of Polytetrafluoroethylene or a similar material (2), the coils (5) (not shown in this figure) are housed or embedded inside the second inner layer or volume in the form of a paraffin-filled bladder (1).

Now that the present invention and its implementation have been sufficiently described, we state that, within its essentiality, the invention may be implemented in other embodiments that present differences in detail with respect to the one indicated as an example, and which will equally receive the protection requested, provided that they do not alter, change or modify its fundamental principle.

The invention claimed is:

1. A device for the treatment of arthritis, arthrosis, chronic inflammations, pain reduction and muscle tension in extremities, which in general has the shape of a case, a glove or a sock, which houses an extremity to be protected, comprising:
a first layer;
a second inner layer or volume in the form of a paraffin-filled bladder, which covers an entire inner space or, partially, areas targeted for treatment, and resistive coils configured to heat the second inner layer;
a thin layer made of latex or an insulating material;
an outer cover that surrounds all the aforementioned layers; and
a control unit configured to turn on and to control temperatures and types of currents to be applied, comprising:
the first layer being made of a porous material;
surrounding the second layer, a splint configured to mount on the extremities, said splint having opposed ends and adjacent edges extending between said opposed ends, said adjacent edges defining an opening with a first distance between said edges; and
bi-metallic wire operatively connected to said splint, said bi-metallic wire configured to contract when electric current is applied drawing said edges towards one another reducing said first distance to a second distance with said splint straightening said extremities.

2. The device for the treatment of arthritis, arthrosis, chronic inflammations, pain reduction and muscle tension in the extremities, according to claim 1, equipped with wires or coils placed between the thin insulating or latex layer and the outer cover, or inside the second layer.

3. The device for the treatment of arthritis, arthrosis, chronic inflammations, pain reduction and muscle tension in the extremities, according to claim 2, wherein the bi-metallic wires are configured to be placed around each finger or toe.

4. The device for the treatment of arthritis, arthrosis, chronic inflammations, pain reduction and muscle tension in the extremities, according to claim 3, wherein the bi-metallic wires are made of woven carbon, nichrome, nitinol or any other conductive element, such that, when heated to a given temperature, the paraffin melts.

5. The device for the treatment of arthritis, arthrosis, chronic inflammations, pain reduction and muscle tension in the extremities, according to claim 4, wherein the control unit of the device comprises:
a switch for turning on and off;
a temperature control knob;
a current control knob for application in electrotherapy;
an electronic circuit wherein the circuit controls the bi-metallic wires of each of the fingers or toes; and
a rechargeable battery and charging point.

6. A device for the treatment of arthritis, arthrosis, chronic inflammations, pain reduction and muscle tension in the extremities, according to claim 1, equipped with bi-metallic wires placed between the thin insulating or latex layer and the outer covering, or inside the second layer.

7. A device for the treatment of arthritis, arthrosis, chronic inflammations, pain reduction and muscle tension in the extremities, according to claim 6, wherein the bi-metallic wires are configured to be placed parallel to the back and the palm of the hand.

8. A device for the treatment of arthritis, arthrosis, chronic inflammations, pain reduction and muscle tension in the extremities, according to claim 7, wherein the bi-metallic wires are made of woven carbon, nichrome, nitinol or any other conductive element, such that, when heated to a given temperature, the paraffin melts.

9. A device for the treatment of arthritis, arthrosis, chronic inflammations, pain reduction and muscle tension in the extremities, according to claim 8, wherein the control unit of the device comprises:
- a switch for turning on and off;
- a temperature control knob;
- a current control knob for electrotherapy application;
- an electronic circuit wherein circuit controls the wires or coils of each of the fingers or toes; and
- a rechargeable battery and a charging point.

10. A device for the treatment of arthritis, arthrosis, chronic inflammations, pain reduction and muscle tension in the extremities, according to claim 1, wherein the splint further includes spaced holes located adjacent said edges, said bi-metallic wire is laced into said spaced holes.

\* \* \* \* \*